United States Patent [19]

Witherspoon et al.

[11] Patent Number: 5,702,358
[45] Date of Patent: Dec. 30, 1997

[54] CARDIOPLEGIA DELIVERY APPARATUS AND METHOD OF USE

[75] Inventors: Leland Witherspoon, Chino Hills; Gerald D. Buckberg, Los Angeles; Paul Akopian, Glendale, all of Calif.

[73] Assignee: Sorin Biomedical Inc., Irvine, Calif.

[21] Appl. No.: 393,317

[22] Filed: Feb. 23, 1995

[51] Int. Cl.$^6$ ................................................ A61M 35/00
[52] U.S. Cl. ........................... 604/4; 128/DIG. 3; 604/67
[58] Field of Search .................................. 604/4, 65, 67, 604/113, 151, 153; 128/DIG. 3; 236/18; 165/132

[56] References Cited

U.S. PATENT DOCUMENTS

| | | | |
|---|---|---|---|
| 3,825,060 | 7/1974 | Heller et al. | |
| 4,065,264 | 12/1977 | Lewis . | |
| 4,282,180 | 8/1981 | Raible . | |
| 4,401,431 | 8/1983 | Arp | 604/4 |
| 4,416,280 | 11/1983 | Carpenter et al. . | |
| 4,427,009 | 1/1984 | Wells et al. . | |
| 4,433,971 | 2/1984 | Lindsay et al. . | |
| 4,466,804 | 8/1984 | Hino | 604/4 |
| 4,512,163 | 4/1985 | Wells et al. . | |
| 4,529,397 | 7/1985 | Hennemuth et al. | 604/4 |
| 4,559,999 | 12/1985 | Servas et al. . | |
| 4,568,330 | 2/1986 | Kajawski et al. . | |
| 4,653,577 | 3/1987 | Noda . | |
| 4,874,359 | 10/1989 | White et al. | 604/4 |
| 4,883,455 | 11/1989 | Leonard . | |
| 5,011,469 | 4/1991 | Buckberg et al. | 604/4 |
| 5,322,500 | 6/1994 | Johnson et al. . | |
| 5,358,481 | 10/1994 | Todd et al. . | |
| 5,385,540 | 1/1995 | Abbott et al. | 604/4 |
| 5,423,749 | 6/1995 | Merte et al. . | |

FOREIGN PATENT DOCUMENTS

PCT/US92/
04028  5/1992  WIPO .

OTHER PUBLICATIONS

A Straight–Forward Approach To Cardioplegia Delivery (2 pages, 1985), Gish Biomedical, Inc.
All–Purpose Cardioplegia Heat Exchanger (5 pages, May 1987), Medtronic Electromedics.
CardioPlegia Over Pressure Valve, (1 page), American Omni Medical, Inc.
The Creation of a Classic. A Precision Engineered Cardioplegia Delivery System, (12 pages, May 1993), Bard Cardiopulmonary Division.
K$^+$ardia Cardioplegia Delivery System, (2 pages, 1993), Cobe Cardiovascular Inc.
New Approaches to Blood Cardioplegic Delivery to Reduce Hemodilution and Cardioplegic Overdose, Kai Ihnken, M.D., Kiyozo Morita, M.D., and Gerald D. Buckberg, M.D., J. Card. Surg., 1994;9:26–36.
Presenting the Sorin BCD Avanced. The Complete Picture of Consistent Performance. (2 pages), Sorin Biomedical, Inc.
Scimed's MYOtherm Cardioplegia System (2 pages).
Single Pass Blood Cardioplegia Systems (2 pages, Oct. 1992), Gish Biomedical, Inc.
With the Monolyth, Superior Performance is a Matter of Course. (10 pages), Sorin Biomedical, Inc.
Coronary Perfusion Pump, Model CP–3000–CD, CP–3000–ID, Tonokura Ika Kogyo Co., Ltd. (product pamphlet/2 pages) undated.

Primary Examiner—John G. Weiss
Assistant Examiner—Ki Yong O
Attorney, Agent, or Firm—Popovich & Wiles, P.A.

[57] ABSTRACT

A cardioplegia delivery device for providing variable ratio delivery of blood and cardioplegia solution to a patient. The device includes separate pumps for crystalloid and blood. A heat exchanger control circuit is provided which includes a heater and an ice bath for warming or cooling the cardioplegia fluid delivered to the patient. The heat exchanger control circuit includes a priming circuit which may be used to purge air bubbles from the circuit.

9 Claims, 11 Drawing Sheets

CARDIOPLEGIA DELIVERY APPARATUS AND METHOD OF USE

FIELD OF THE INVENTION

This invention relates to apparatus and methods used in the administration of blood and cardioplegia solutions during cardiac surgery. More particularly, the invention is directed to a cardioplegia delivery device which may be used to deliver variable ratios of blood and cardioplegia solution at a controlled temperature.

BACKGROUND OF THE INVENTION

During open-heart surgery the blood of the patient is bypassed to an extracorporeal support system which supplies the pumping function of the heart and the oxygenation function of the lungs. This effectively isolates the heart enabling the surgeon to make the necessary repairs to the heart. During the surgery it is desirable to arrest the beating pumping action of the heart. It is also important during the time that the heart is isolated from the blood supply circuit that the heart be protected from ischemia or lack of blood flow which can result in permanent damage to the heart.

It is well known that the heart may be protected during open heart surgery by utilizing a technique commonly known as cold cardioplegia. This involves administering to the heart a cooled cardioplegia fluid which may consist of a crystalloid chemical solution containing potassium and other additives or a mixture of the crystalloid solution with blood. Use of a cooled cardioplegia fluid comprising a mixture of oxygenated blood and crystalloid solution is known to be effective in keeping the heart attested while at the same time keeping the heart oxygenated. Cardioplegia fluid is cooled by utilizing a cardioplegia delivery system which includes a heat exchanger.

As an alternative to cold cardioplegia, it is sometimes desirable to utilize a technique known as warm cardioplegia. In this technique the cardioplegia fluid is not cooled and, consequently, it is not necessary to use a heat exchanger in the cardioplegia delivery system. This technique involves supplying a cardioplegia fluid mixture of warm oxygenated blood and cardioplegia solution throughout the cardiac surgery. This technique has gained acceptance among some surgeons as a safe and effective means of arresting and protecting the heart during surgery.

During surgery where warm cardioplegia is the technique utilized it sometimes becomes necessary to convert to cold cardioplegia in order to cool the heart. In such circumstances it is necessary to connect a heat exchanger in the cardioplegia delivery circuit if one is not present so that the cardioplegia fluid may be cooled. In prior cardioplegia delivery systems the conversion from warm cardioplegia to cold and vice versa has been cumbersome and inaccurate. Therefore, it would be desirable to provide a cardioplegia temperature control device which is accurate and easy to use during such a conversion. In addition, it would be desirable if the device could be used during either cold or warm cardioplegia delivery to more precisely control the temperature of the cardioplegia fluid as it is delivered to the patient and to convert back and forth from cold to warm cardioplegia.

Whether warm cardioplegia or cold cardioplegia is prescribed by the physician, the manner of administration of the cardioplegia fluid during surgery is similar. Cardioplegia delivery systems include components which supply blood and cardioplegia solution, mix the desired ratio of blood cardioplegia solution and then supply the mixture to the patient's heart. A heat exchanger is often included in the system to warm or cool the cardioplegia fluid. A specific ratio of oxygenated blood with cardioplegia solution containing potassium and other additives is delivered to the coronary arteries. The term cardioplegia fluid, as used herein, shall mean any ratio of blood to cardioplegia solution and shall include 100% blood or 100% cardioplegia solution. Once the heart is arrested, the delivery system continues to supply the cardioplegia fluid to keep the heart arrested and to deliver oxygen into the myocardium. Pressures and temperatures are monitored to avoid damage to the heart. At the end of the bypass procedure, 100% blood is commonly administered to flush the cardioplegia solution out of the myocardium allowing the heart to be returned to its normal sinus rhythm.

The ratio of blood to cardioplegia solution which is delivered during the course of surgery varies according to the progress of the surgery and the condition of the heart. In the past it has been difficult to accurately adjust the ratio of blood to cardioplegia solution during the surgery. Thus, it would be desirable to provide a delivery device which is able to provide a variable ratio of cardioplegia solution to blood and which may be quickly and easily changed during the course of the surgery without the necessity of disconnecting hoses or otherwise disabling the delivery circuit.

SUMMARY OF THE INVENTION

In accordance with the present invention there is disclosed a variable ratio delivery device for delivering blood and cardioplegia solution from separate sources for delivery to a patient. The device comprises a first pump connected to a cardioplegia solution source to cause cardioplegia solution to flow through the first pump and a second pump connected to the blood source to cause blood to flow through the second pump. A pump controller is provided for adjusting the rate of flow of cardioplegia solution through the first pump and the rate of flow of blood through the second pump until a selected ratio is achieved. The device may further include a pressure sensor for sensing the pressure of the combined blood and cardioplegia solution at the delivery site. The sensed pressure may be antegrade pressure or retrograde pressure. The device may be programmed with a high pressure limit for either retrograde or antegrade pressure. In either case the pump controller is responsive to a sensed pressure which is above the upper limit to adjust the rate of flow through at least one of the first and second pumps, stop at least one of the first and second pumps, or sound an alarm.

The device may also be programmed with a low pressure limit for either antegrade or retrograde pressure. In that case the pump controller is responsive to a sensed pressure which is below the lower limit to adjust the rate of flow through at least one of the first and second pumps, stop at least one of the first and second pumps, or sound an alarm.

In another aspect the invention is a device for controlling the temperature of a heat exchange liquid such as water which is circulated through a heat exchange liquid flow path of the heat exchanger used for warming or cooling blood or cardioplegia fluid. The cardioplegia fluid may comprise blood, cardioplegia solution or a mixture thereof. The device comprises a reservoir which holds cooled water, a heater which has an inlet connected to receive water from the reservoir and an outlet connected to a water inlet of the heat exchanger. A first valve is included and has an input connected to receive water from the outlet of the heat exchanger and has a first outlet connected to the reservoir and a second outlet connected to deliver water to the input of the heater.

The valve is controllable such that either of the first and second outlets is selectable. The device further includes a pump connected to move water from the reservoir through the heater and heat exchanger and back to the reservoir when the first outlet of the first valve is selected and to recirculate water through the heater and heat exchanger in a manner that bypasses the reservoir when the second outlet of the first valve is selected. The device may further comprise a pump controller for adjusting the rate of flow of heat exchange liquid through the pump. A temperature sensor may be provided for sensing temperature of water delivered to or flowing from the heat exchanger or of blood or cardioplegia solution delivered to or from the heat exchanger. If such a temperature sensor is provided the pump controller is responsive to the sense temperature to adjust the rate of flow of water through the pump. In this embodiment the device may further include a heater controller for adjusting the temperature of the heater. A temperature sensor may be provided to sense the temperature of water delivered to or from the heat exchanger, or blood or cardioplegia fluid delivered to or flowing from the heat exchanger with the heater controller being responsive to the sense temperature to adjust the temperature of the heater upward if the sensed temperature is less than a selected temperature and to adjust the temperature of the heater downward if the sensed temperature exceeds the selected temperature. The device may further include a controller connected to the pump, first valve and heater, the controller being operative to selectably control the flow of water through the pump, the temperature of the heater and to select the first or second output of the first valve as the flow path. This embodiment may further include a temperature sensor to sense temperature of the water delivered to or exiting from the heat exchanger, or blood or cardioplegia fluid delivered to or flowing from the heat exchanger with the controller being responsive to the sensed temperature to adjust the flow of heat exchange fluid through the pump, the temperature of the heater, and to select either the first or second valve outlets of the first valve in order to maintain the temperature of the blood or cardioplegia fluid at a desired value.

This embodiment of the invention may further include a priming circuit which comprises a priming line connected at one end to receive heat exchange liquid flow from the pump and at the other end to deliver heat exchange liquid to the cool water reservoir. The device may further include a second valve connected in the priming line and at least one bubble located to sense the presence of air bubbles in the flow of heat exchange liquid through the pump. The controller is connected to receive the signal from the bubble sensor and to respond to sensed air bubbles to close the first valve and open the second valve which causes heat exchange liquid to circulate in a loop from the pump to the cool water reservoir and back until air bubbles are purged through the pump.

In a further embodiment the invention is a device for delivering a variable ratio of blood from a blood source and cardioplegia solution from a cardioplegia solution source to a heat exchanger for delivery to a patient and for providing temperature controlled water to circulate through a water flow path of the heat exchanger for controlling the temperature of the blood and cardioplegia solution mixture provided to the patient. The device comprises first and second pumps having inlets connected to receive cardioplegia solution and blood respectively. The device further includes a pump controller which adjusts the rate of flow of the cardioplegia solution and blood through the first and second pumps until a desired ratio is achieved. A reservoir is provided to hold cooled heat exchange liquid. The device includes a heater having an inlet connected to receive heat exchange liquid from the reservoir in an outlet connected to a heat exchange liquid inlet of the heat exchanger. A valve is provided having an input connected to receive heat exchange liquid from a heat exchange liquid output of the heat exchanger and having a first outlet connected to the reservoir and a second outlet connected to deliver heat exchange liquid to the input of the heater. The valve is controllable such that either the first or second outlet of the valve is selectable. A pump is connected to move heat exchange liquid from the reservoir through the heater and heat exchanger and back to the reservoir when the first outlet of the valve is selected and to recirculate heat exchange fluid through the heater and heat exchanger when the second outlet of the valve is selected.

In still a further embodiment the invention is a method for delivering a variable ratio cardioplegia fluid to a patient. The method comprises providing a source of cardioplegia solution and a source of blood. The method includes connecting the source of cardioplegia solution to a first pump having a variable flow rate and connecting the source of blood to a second pump having a variable flow rate. The flow rates of the first and second pumps are adjusted to obtain the desired blood, cardioplegia solution ratio. The blood and cardioplegia solution are combined and delivered to the patient.

In another aspect the invention is a device for supplying heat exchange liquid to a heat exchanger used in an extracorporeal circuit for warming or cooling blood. The device includes a first reservoir to hold a volume of cooled heat exchange liquid and a second reservoir positioned adjacent the first reservoir in a location that will catch heat exchange liquid from the first reservoir should the first reservoir develop a leak. Usually, the second reservoir is positioned below and around the first reservoir. The second reservoir is sized to hold a volume of heat exchange liquid which is at least as great as the volume of heat exchange liquid in the first reservoir. The device includes a pump connected to move heat exchange liquid from the first reservoir to the heat exchanger.

In another embodiment the invention is a device for supplying heat exchange liquid to a heat exchanger used in an extracorporeal circuit for warming or cooling blood. The device comprises a reservoir to hold cooled heat exchange liquid having inlet and outlet connections for connecting with the heat exchanger. A pump is provided to move heat exchange liquid from the reservoir through the outlet connection to the heat exchanger and back to the reservoir through the inlet connection. A connection sensor is connected to the outlet and inlet of the reservoir to sense whether the heat exchanger is connected to the inlet and outlet and to provide a signal indicative thereof. A pump controller is provided for turning the pump on and off and is connected to receive the signal from the connection sensor and responsive to turn the pump off if the presence of the heat exchanger is not sensed.

BRIEF DESCRIPTION OF THE DRAWINGS

The foregoing and other aspects of the present invention will be best appreciated with reference to the detailed description of the invention which follows when read in conjunction with the accompanying drawings wherein.

DETAILED DESCRIPTION OF THE INVENTION

Cardioplegia Delivery Device

Figure 1:
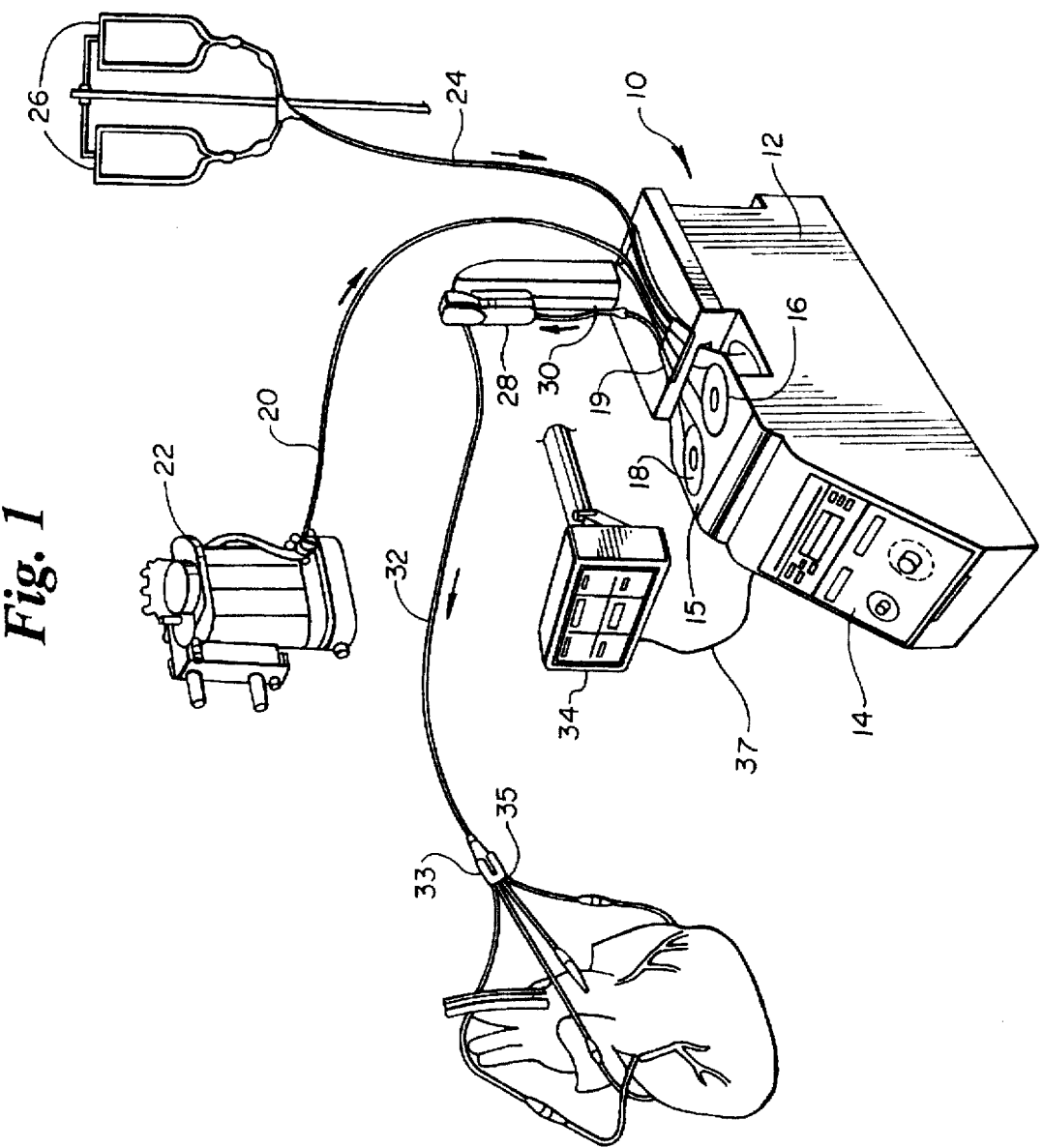
FIG. 1 is a schematic view of a cardioplegia delivery system which includes a cardioplegia delivery device with a remotely located display panel in accordance with the present invention.
Figure 2:
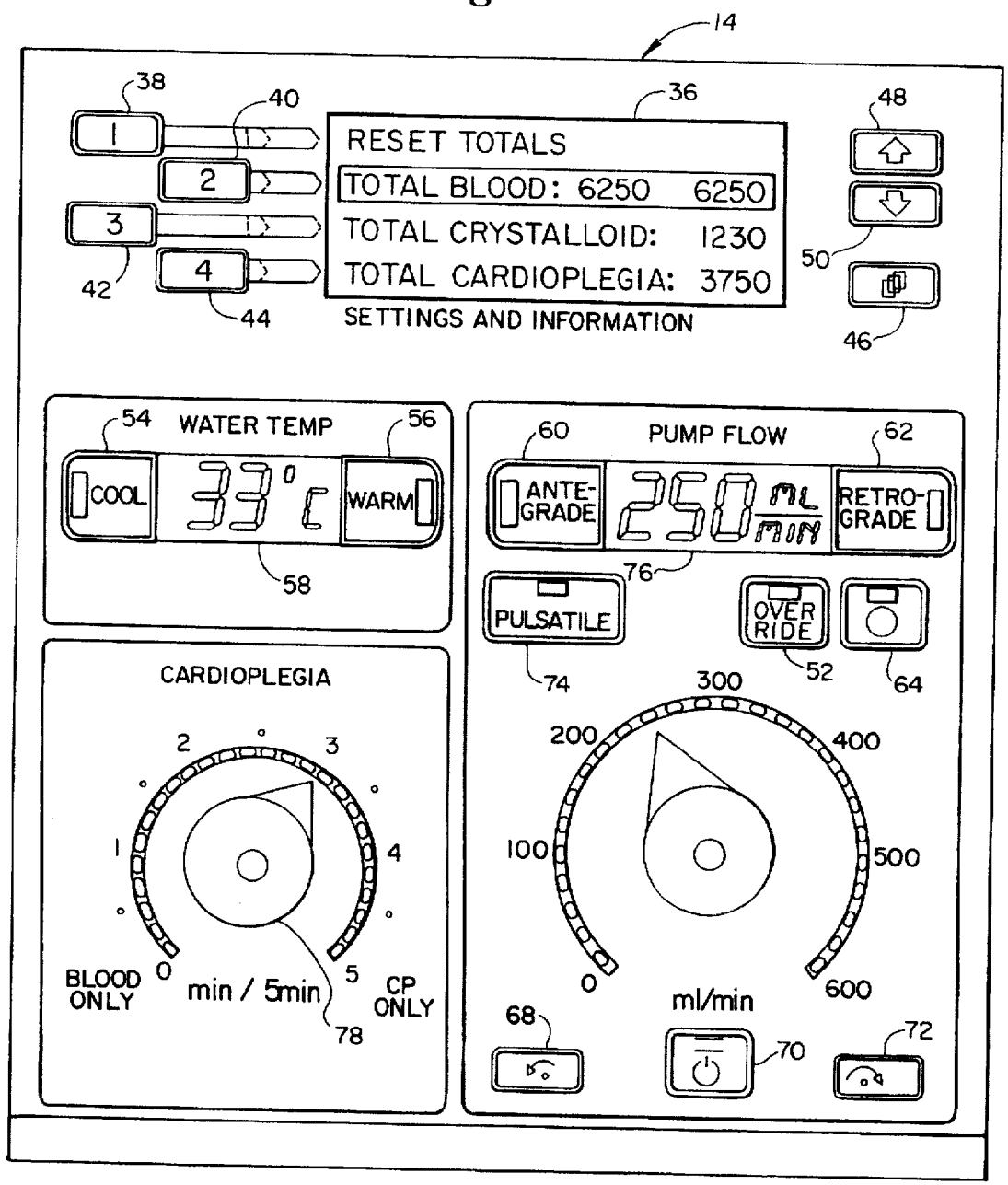
FIG. 2 is a plan view of the control panel of the cardioplegia delivery device.

The cardioplegia delivery device of the present invention can be understood generally with reference to FIGS. 1-4. FIG. 1 is a schematic view of a cardioplegia delivery system which includes a cardioplegia delivery device 10 in accordance with the present invention. Device 10 includes a housing 12 with a control panel 14. A more detailed view of control panel 14 is shown in FIG. 2 which is discussed in more detail hereafter.

Device 10 includes a pumping mechanism comprised of a crystalloid pump 16 and a blood pump 18. In the embodiment disclosed pump 16 and 18 may be three inch roller pumps although other types of controllable pumping mechanisms with variable flow rates such as centrifugal pumps or infusion or syringe type pumps may be utilized. The pumps are covered with a cover 15 which is preferably transparent.

Blood is supplied to blood pump 18 through a blood supply line 20 which is laid through a tubing organizer 19 and inserted into the raceway of blood pump 18. Supply line 20 is connected to a suitable blood source such as an arterial blood reservoir or the output of a blood oxygenator 22 as shown in this embodiment. Crystalloid pump 16 is similarly supplied with cardioplegia solution through cardioplegia supply line 24 from at least one cardioplegia solution source 26. In the embodiment disclosed two cardioplegia solution sources 26 are used. The sources may contain identical cardioplegia solution or one source may contain a cardioplegia solution having a higher concentration of potassium than the other. The higher concentration may be used initially with the lower concentration source being used after the heart has been arrested. After each has passed through its respective pump, the blood and cardioplegia solution supply lines merge into a single delivery line 30 that is placed in the tubing organizer and attached to an inlet of heat exchanger 28. As will be described in more detail hereafter in use, the operator may choose to use only the blood pump, only the crystalloid pump or both the blood and crystalloid pumps. Since the speed of the pumps and, consequently, the flow of fluids through the pumps is independently selectable any number of different ratios of blood to cardioplegia solution may be selected.

Heat exchanger 28 may be mounted directly on cardioplegia delivery device 10 as in the embodiment disclosed or may be mounted in a remote location. As shown, heat exchanger 28 is mounted directly on heat exchange liquid outlet and inlet ports mounted to the housing of device 10. The heat exchange liquid inlet and outlet ports of device 10 mate with matching outlet and inlet ports on heat exchanger 28 so that heat exchange liquid can be circulated through a heat exchange liquid flow path within heat exchanger 28. The heat exchange liquid flow path is in heat exchange relationship with the cardioplegia fluid flow path through the heat exchanger. The heat exchange liquid may be any suitable liquid, typically water. After the cardioplegia fluid has passed through heat exchanger 28 it is delivered to the heart of the patient through cardioplegia patient delivery line 32. Delivery line 32 runs to a junction 33 at which point a number of antegrade and retrograde feed cannulas are used to transport the cardioplegia fluid to the patient's heart. At least one pressure sensor 35 is located at the junction 33 to measure antegrade and retrograde line pressures.

Figure 10:
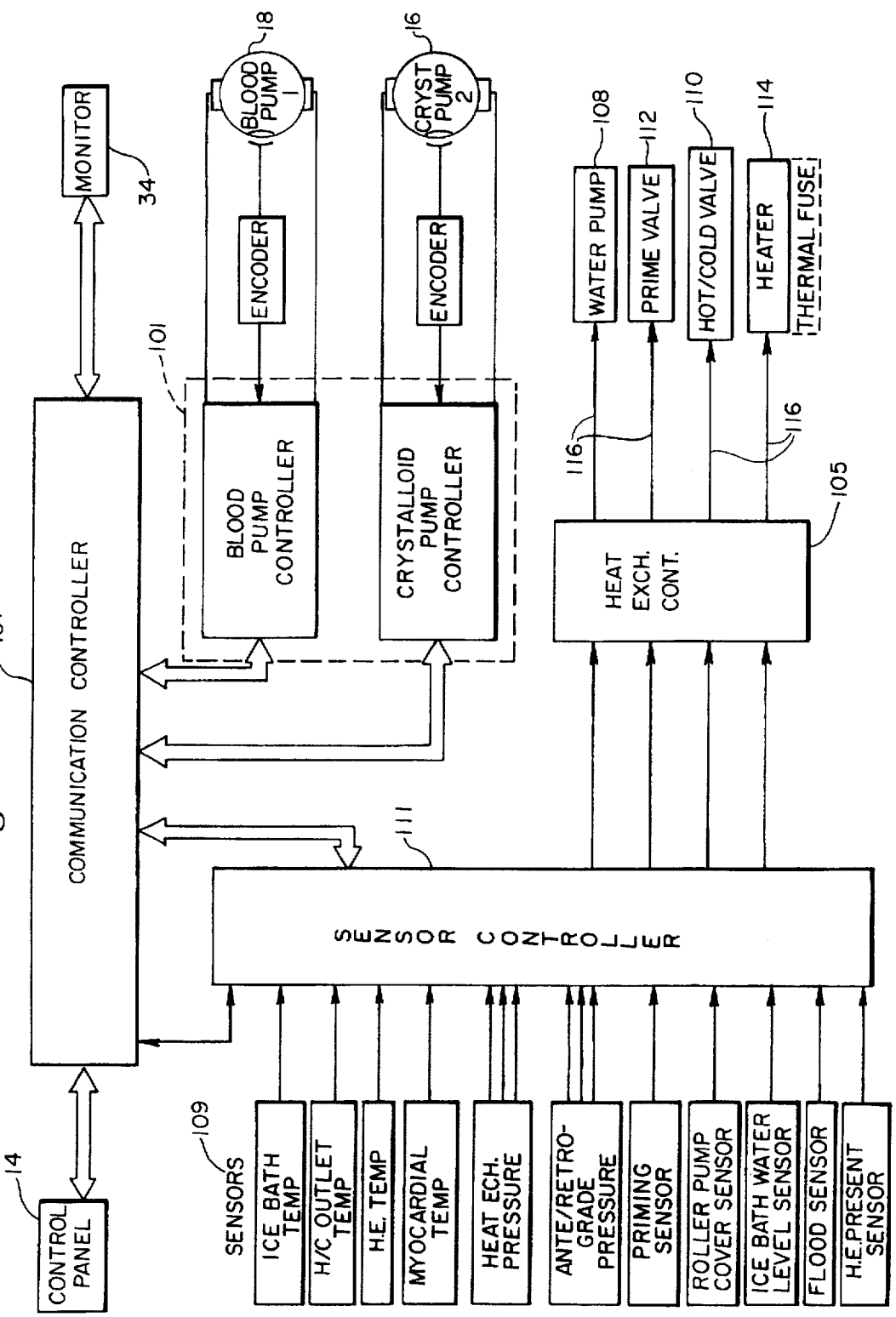
FIG. 10 is a function block diagram of the control circuit of the cardioplegia delivery device of the present invention.

The device is also provided with sensors at the water connection inlet and outlet which sense the presence of the heat exchanger. As seen in FIG. 10 the sensors are connected to sensor controller 111 and cause the water pump in the heat exchange control circuit to stop if the heat exchanger is not sensed. In the absence of this feature water can inadvertently be pumped out of the water connectors if the device is energized without the heat exchanger in place. This can cause significant problems which are eliminated with this feature.

The cardioplegia delivery device may be connected by an electrical cable 37 to a remotely located display panel 34 which may display flow rate, pressure at the heat exchanger, pressure at the antegrade cannula, or pressure at the retrograde cannula and ischemic time in ischemic intervals or total ischemic time. The remote display may also display other information such as myocardial temperature or heat exchanger temperature, cardioplegia dose volume (current dose or sum of doses) and a dose timer.

Figure 3:
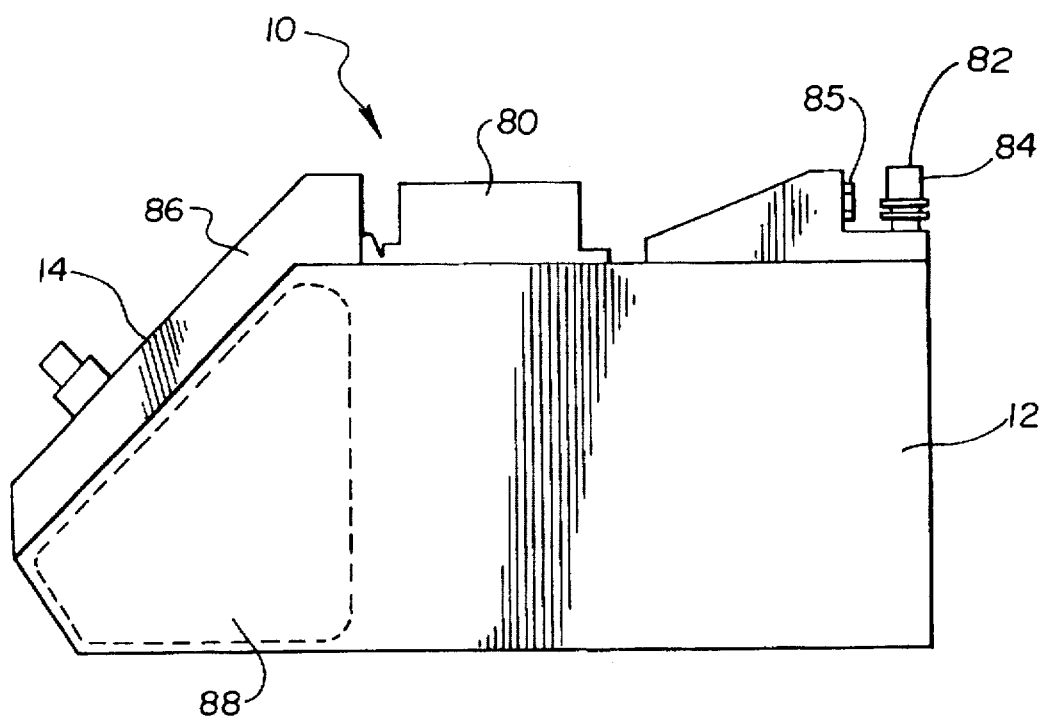
FIG. 3 is a side view of the cardioplegia delivery device.
Figure 4:
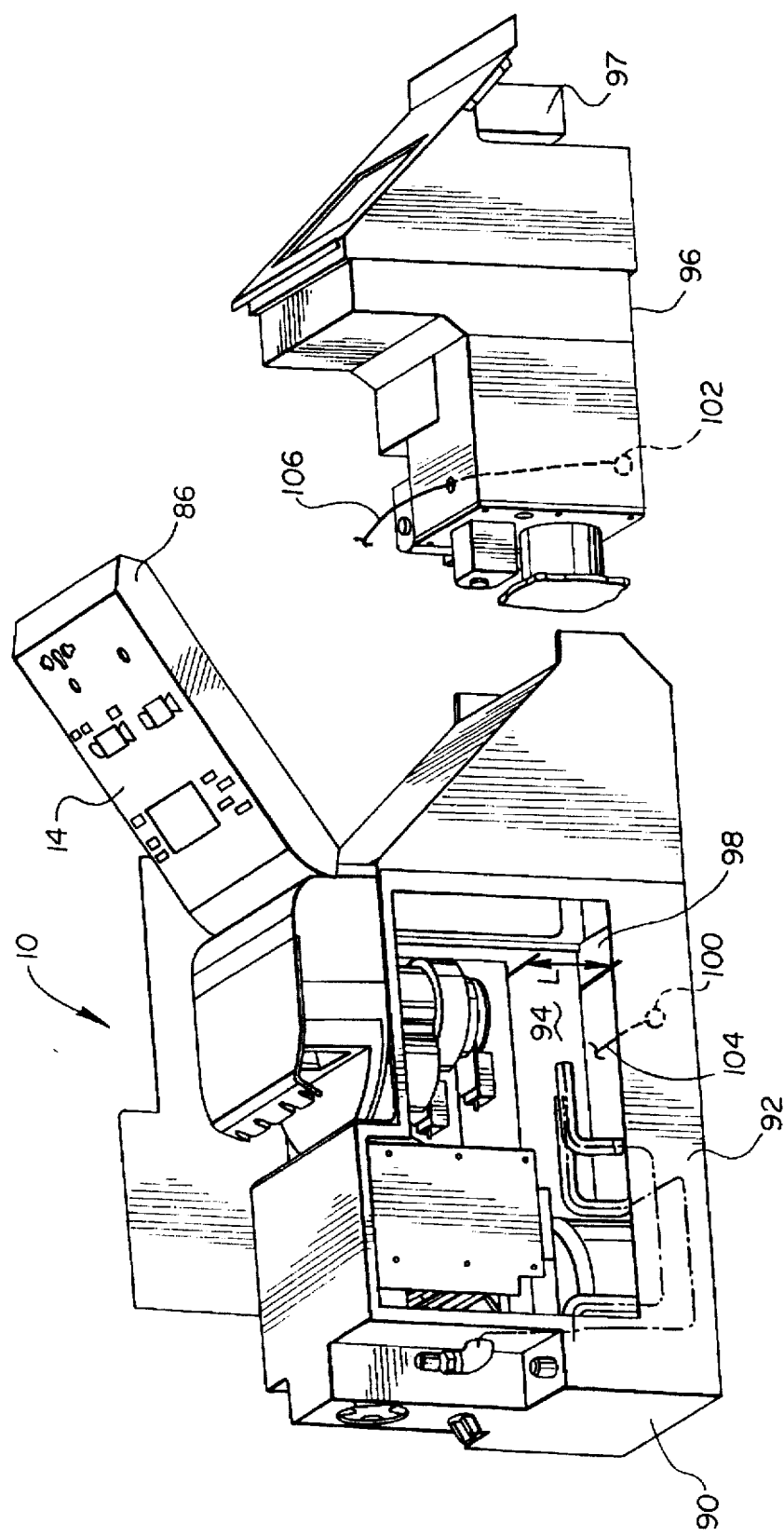
FIG. 4 is a partial perspective view of an unassembled portion of the cardioplegia delivery device.

The component and control configurations of cardioplegia delivery device 10 are shown in more detail in FIGS. 2, 3 and 4. FIG. 2 is an enlarged view of the control panel 14 which will be discussed in more detail hereafter. FIG. 3 is a side view of the cardioplegia delivery device. The blood and crystalloid pumps are contained within a pump housing 80 located on the top of housing 12. A pair of water (heat exchanger liquid) connectors (inlet/outlet) 82, 84 are located near the back of housing 12. A number of pressure sensor and temperature sensor connectors 85 are positioned at the top of the housing to allow remote sensors to be connected to the device. For example, the device may have sensors to monitor line (blood) pressure at the heat exchanger and at the antegrade and retrograde cannulas. Temperature sensors may be located on the myocardium and at the heat exchanger. The heat exchanger may be mounted directly on the connectors by mating the heat exchanger inlet and outlet to the connectors. Alternatively, the heat exchanger may be mounted to a separate mast mounted holder and connected to the water connectors with a set of separate water hoses. At the front of the device is a front panel 86 on which control panel 14 is mounted. Front panel 86 may be hinge mounted at the top of housing 12 to allow access to the cool water reservoir (ice bath) 88. The reservoir has at least one spillover drain which can be connected to a sink or otherwise to allow the reservoir to partially drain. This allows the operator to add ice as needed without overflowing the reservoir.

Secondary Containment Reservoir

FIG. 4 shows the location of an added safety and performance feature incorporated into the device. The device is equipped with a secondary containment reservoir to catch and hold any or all of the contents of the cool water reservoir should a leak develop. The secondary containment reservoir is bounded on three sides by end portion 90 and side portions 92 and 94 and on the bottom by bottom portion 98. When front section 96 of the device is fit into the housing a water tight seal is made at the fourth side of the secondary containment reservoir which encloses a volume to a depth L defined by the minimum height of side portions 92 and 94. Depth L is chosen so that the bounded volume will hold the entire contents of the cool water reservoir. The cool water reservoir is located in front section 96 and any water which leaks out will be caught in the containment reservoir before it leaks to the floor. The containment reservoir is isolated from the electronics so that no safety or performance problems are created.

The device is also equipped with an overflow reservoir 97 positioned adjacent the cool water reservoir 88. If the cool water reservoir is overfilled the excess water will spill over and be retained by overflow reservoir 97. The device is also provided with flood sensors 100 and 102 which are connected through wires 104 and 106 to a sensor controller (FIG. 10). Flood sensors 100 and 102 are located in lower portions of the housing where water tends to puddle if a leak occurs. The flood sensors detect the presence of water leaks and cause the water pump to shut down and also cause an alarm to warn the operator should a leak occur

Variable Ratio Cardioplegia Delivery

Figure 5:
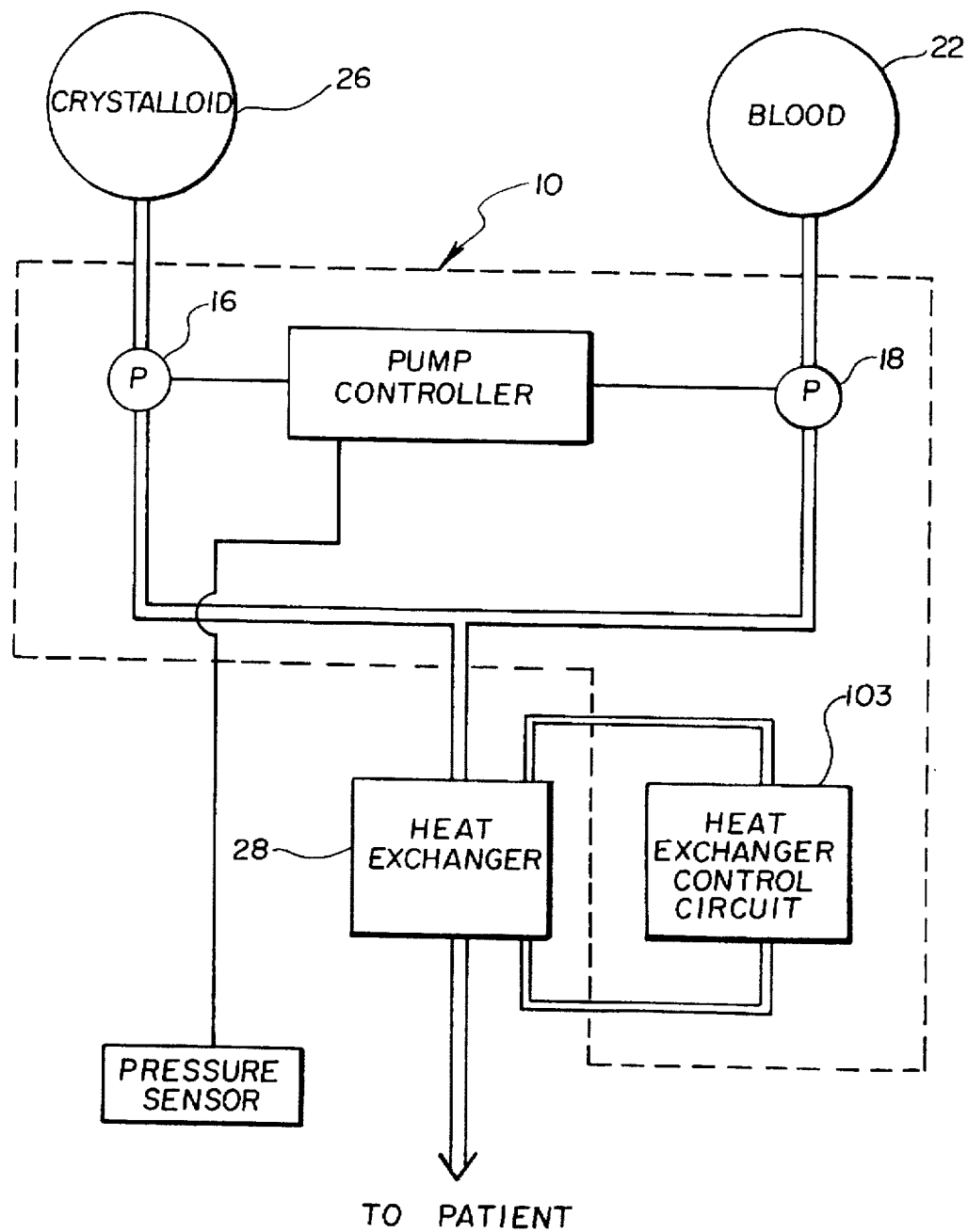
FIG. 5 is a functional block diagram of the cardioplegia delivery system including the cardioplegia delivery device of the present invention.

The variable ratio cardioplegia delivery features of the present invention can best be understood with reference to FIG. 5 which is a functional block diagram of the cardioplegia delivery device. Those components contained within device 10 are enclosed with a dashed line. Variable ratio delivery is one of the primary features of the invention and is achieved by providing a separate crystalloid pump 16 and blood pump 18, each of which may be independently controlled by a pump controller 101 in a coordinated manner to achieve a selectable accurate ratio of blood to cardioplegia solution which can be varied as needed throughout the course of the surgery.

In a manner which will be described in more detail hereafter the operator is able to select flow parameters including flow rate and the ratio of blood to cardioplegia solution. These parameters are set at the control panel 14 and as seen in FIG. 10 are communicated through a commtmication controller 107 to the pump controller 101 which consists of a blood pump control and a crystalloid pump control. The RPM's of the pumps and consequently the flow rates, are adjusted by the pump controller so that the selected flow and ratio parameters are achieved.

Heat Exchanger Liquid Temperature Control

Another significant aspect of the present invention is the ability to supply on demand either cool or warm water to the heat exchanger. This is achieved by providing the heat exchanger control circuit 103 shown in FIG. 5.

Figure 6:
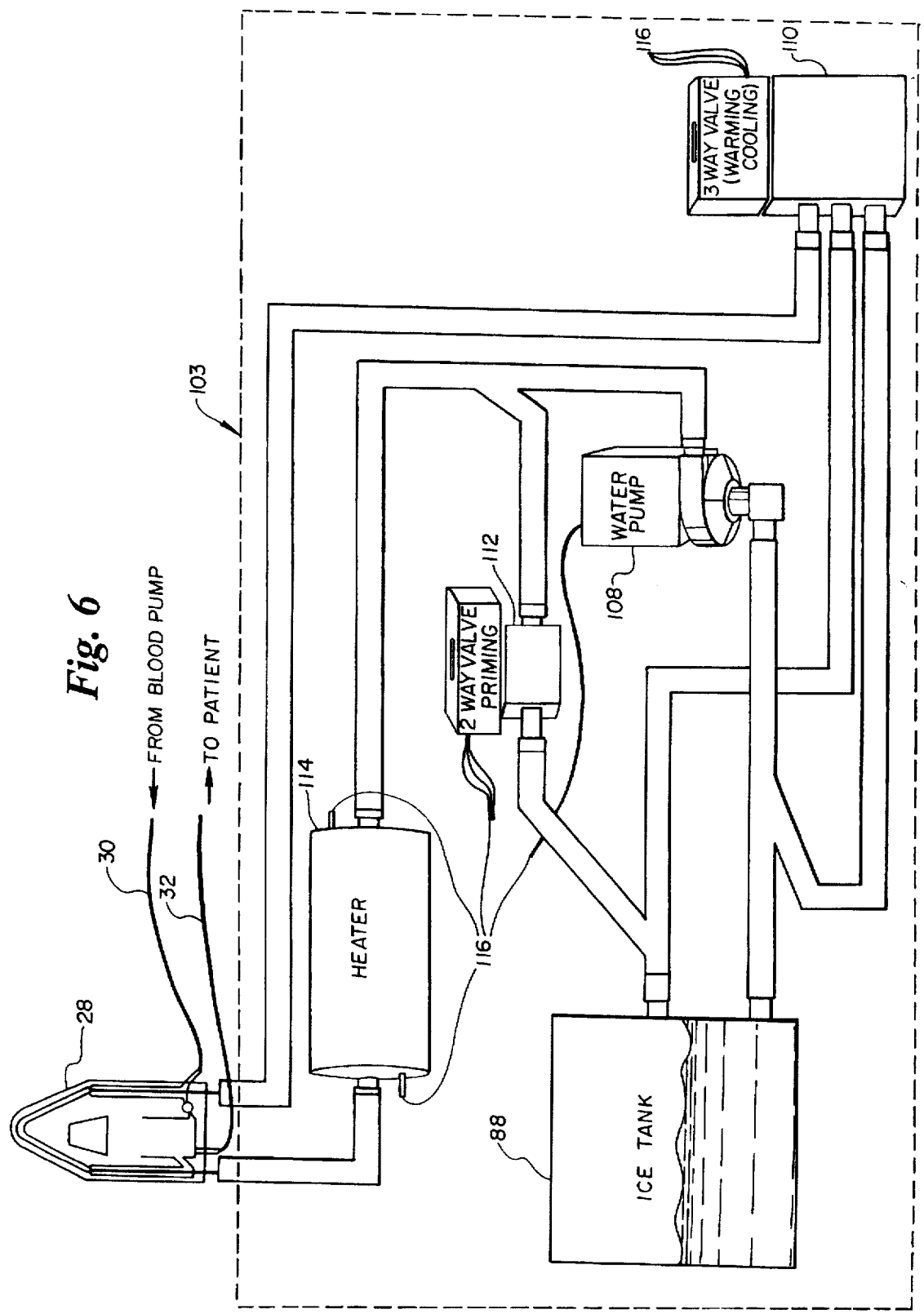
FIG. 6 is a schematic diagram of the heat exchange control circuit of the present invention.

The heat exchange controller is shown in more detail in FIG. 6 which is a schematic diagram of the components of the control circuit and their connection. The heat exchanger control circuit includes cool water reservoir 88, a water pump 108, a three-way valve 110, a two-way valve 112, and a heater 114. Control lines 116 connect the heater, valves and water pump to a heat exchange controller 105 (FIG. 10) which communicates with the control panel and various sensors 109 through sensor controller 111 to control the flow of cool or warm water through the heat exchanger.

In a manner which will be described in more detail hereafter the operator is able to select at the control panel whether cool water or warm water is delivered to the heat exchanger. The temperature of the warm water may be set within a range of 4° C. to 40° C. and the heater is controlled to warm the water to the selected temperature before it enters the heat exchanger. The temperature of the cool water is dependent on the temperature of the cool water reservoir which is typically kept between 0° C. and 4° C. by adding ice to the reservoir.

Figure 7:
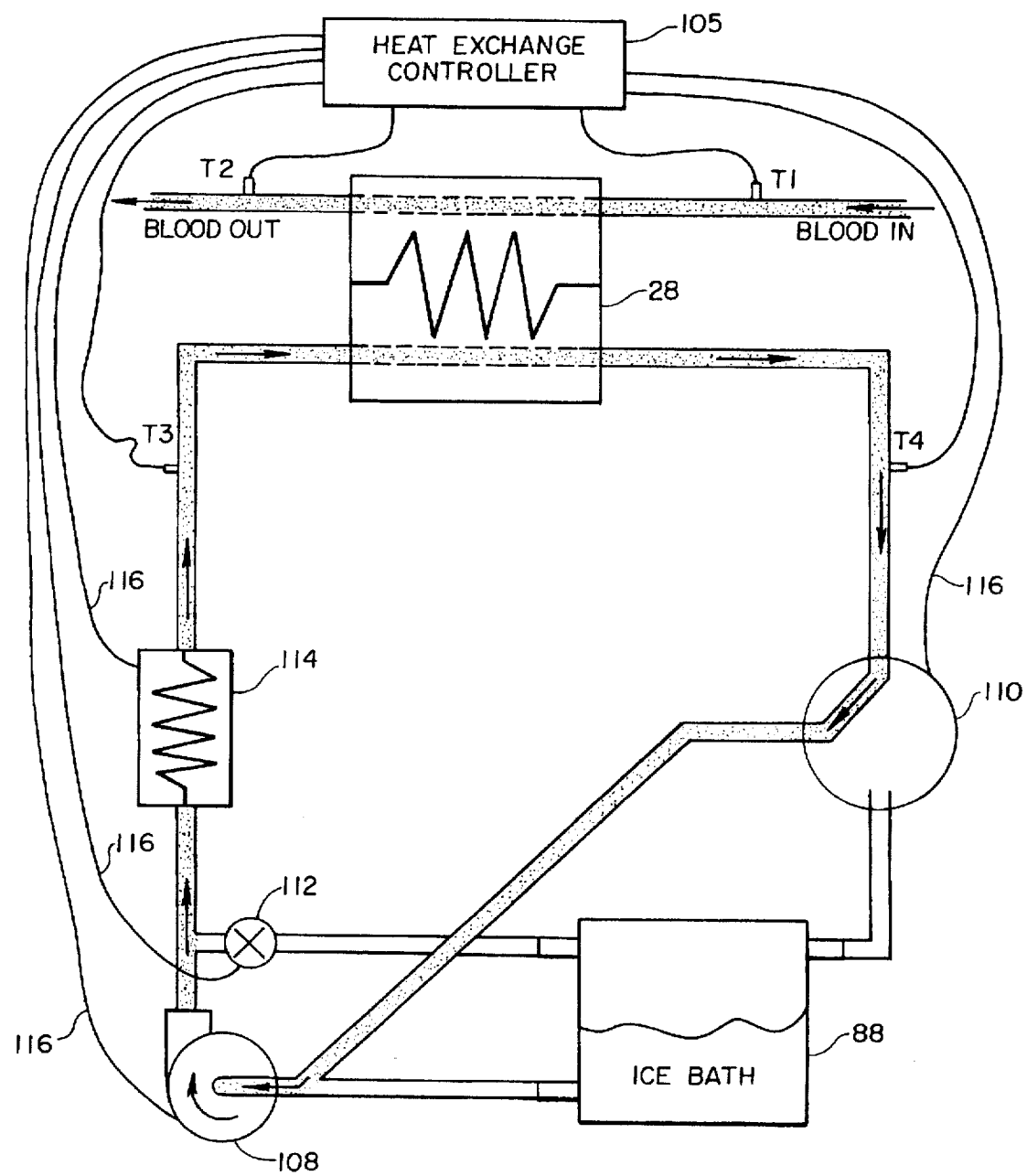
FIG. 7 is a diagram of the water flow path of the heat exchange control circuit during blood warming.
Figure 8:
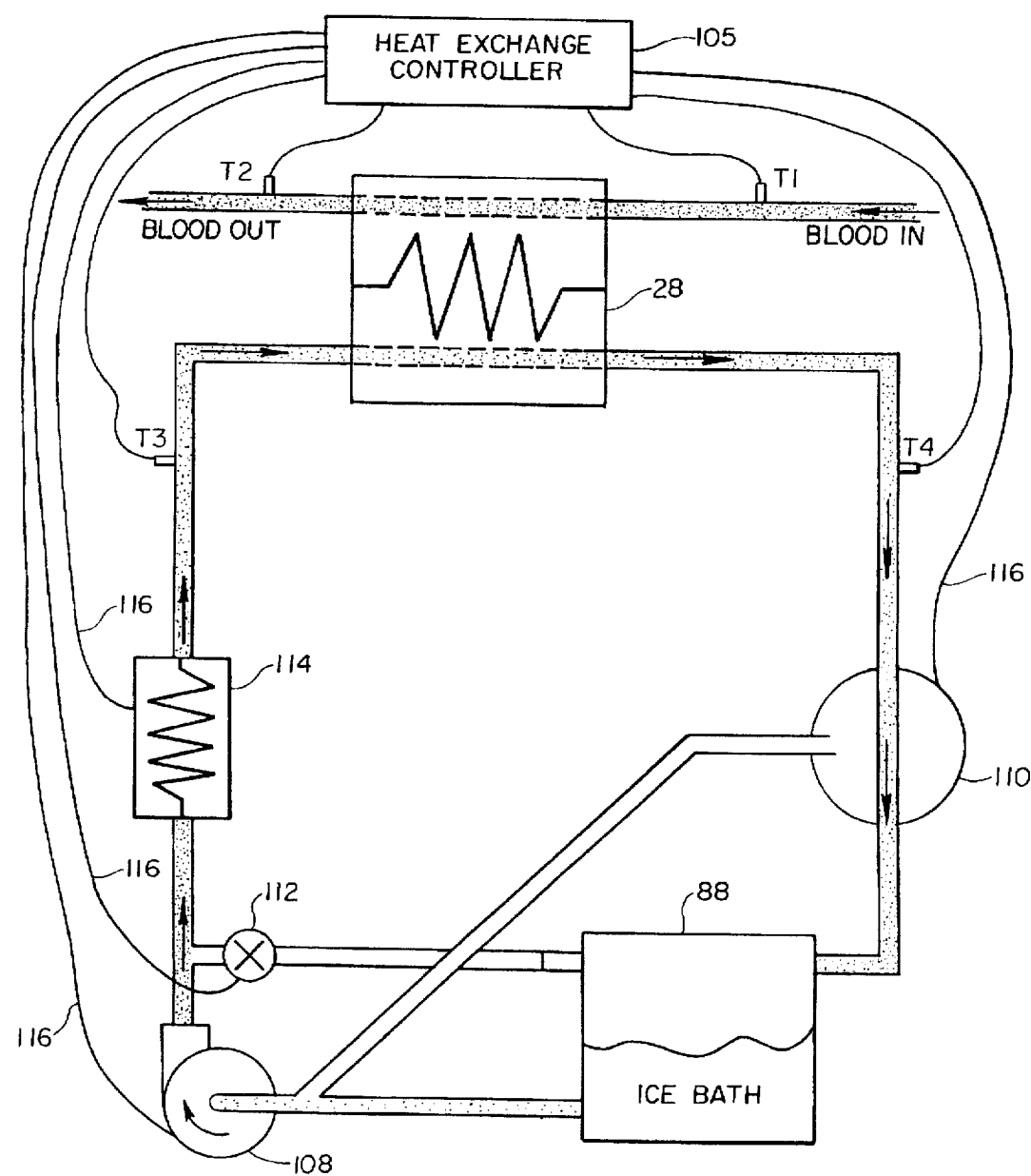
FIG. 8 is a diagram of the water flow path of the heat exchange control circuit during blood cooling.

FIGS. 7 and 8 show the flow path of water through the heat exchanger when wann water is supplied (FIG. 7) and cool water is supplied (FIG. 8). As seen in FIG. 7 when the operator selects warm water, three-way valve 110 is selected to bypass cool water reservoir 88 so that the water in the circuit is recirculated around a loop which includes water pump 108, heater 114 and heat exchanger 28. The heat exchange controller is connected to sensors T3 and T4 which monitor the temperature of the water as it enters and exits the heat exchanger. Sensors $T_1$ and $T_2$, also connected to the heat exchange controller, measure the temperature of blood as it enters and exits the heat exchanger. These temperatures may be displayed on the control panel or remote display to provide additional information. The heat exchange controller 105 adjusts the temperature of heater 114 and the speed of water pump 108 based upon the sensed temperatures. By controlling the speed of the water pump and the temperature of the heater the rate of flow and temperature of water flowing through the heat exchanger is more precisely controlled. This results in more accurate control of the temperature of cardioplegia fluid delivered to the patient.

If the operator has selected cool water to be circulated through the heat exchanger as in FIG. 8, the three-way valve is operated to circulate water through the cool water reservoir 88. In this case although there is flow through the heater it is not energized and does not heat the water which passes through. Thus, the temperature of cool water passing through the heat exchanger depends on the temperature of the water in the cool water reservoir and the water flow rate.

It will be apparent that although the heat exchange control circuit disclosed herein is used in a cardioplegia delivery circuit it would be equally advantageous used in other situations. For example it could be used any time a heat exchanger is used in extracorporeal blood circuits to warm or cool blood.

Water Pump Priming Circuit

Figure 9:
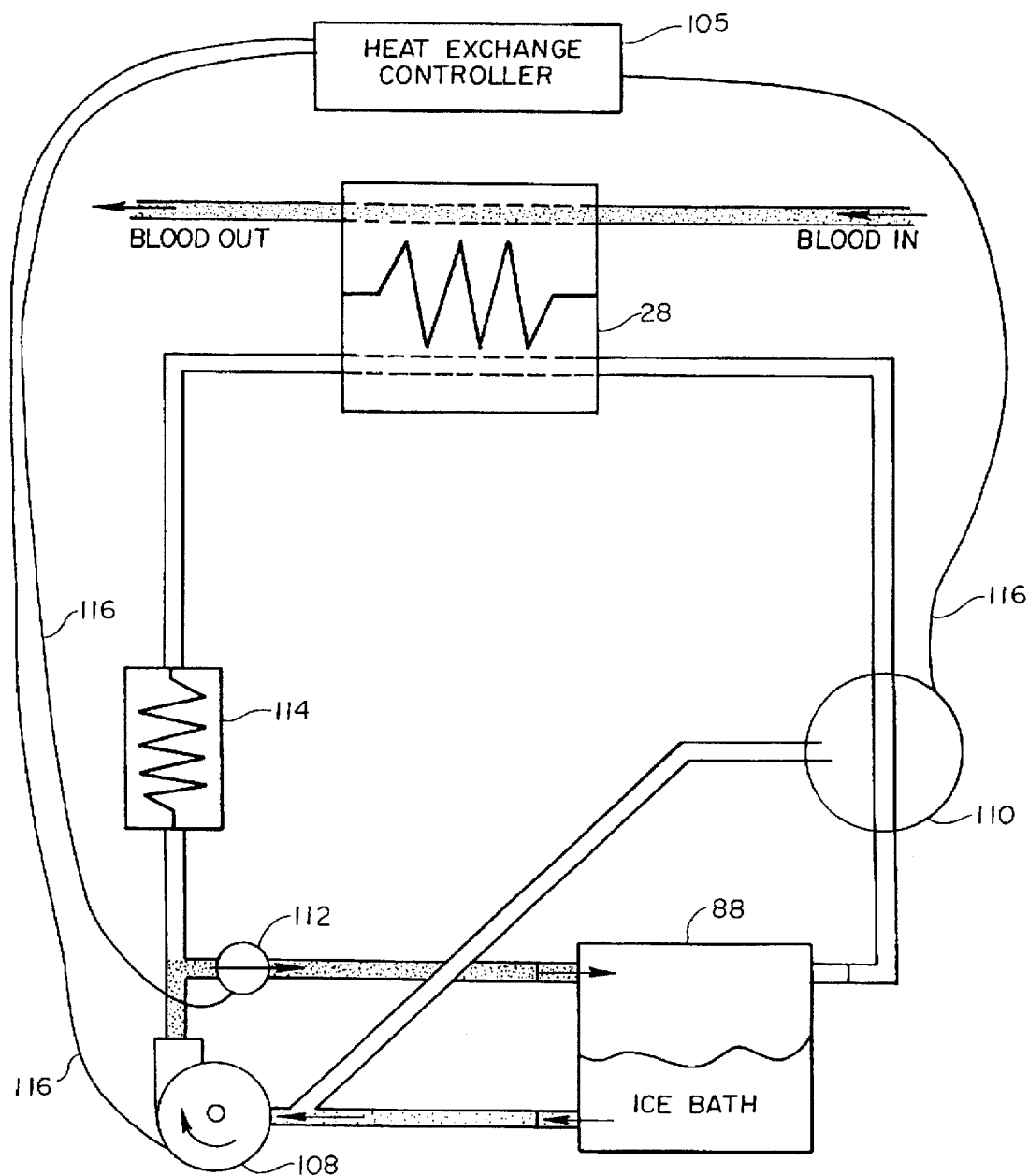
FIG. 9 is a diagram of the water flow path of the heat exchange control circuit during priming.

FIG. 9 is a diagram of the flow path of water when the water pump priming feature of the invention is activated. The heat exchange circuit is provided with at least one bubble sensor B1 which may be located at the output of pump 108. Additional bubble sensors may be located elsewhere in the circuit and preferably may be combined with temperature sensors $T_3$ and $T_4$. If any of the bubble sensors detect air in the circuit that information is provided to the heat exchange controller which opens two-way valve 112 and closes three-way valve 110. This results in the flow path shown in FIG. 9 which circulates the water around a closed loop until the water pump has purged the air from the circuit. When all the air has been removed the two-way valve closes and the three-way valve opens to resume delivery of warm or cool water to the heat exchanger as selected.

Operation of the Cardioplegia Delivery Device a. Pressure Control

The operation of the cardioplegia delivery device can be best understood with reference to FIG. 2 which is a view of the operator control panel 14. Control panel 14 can be seen to consist of numerous sections. Across the top is and LCD display 36 which shows 4 lines of settings and information. Pushbuttons 38, 40, 42, and 44 are used to select one of the four lines of information on the display. A menu pushbutton 46 may be used to scroll-through different menu pages. Once the operator has selected the desired menu page with pushbutton 46 and the desired line with pushbuttons 38, 40, 42, and 44, pushbuttons 48 and 50 are used to adjust the values (increase/decrease) found in the display. Using this process the operator is able to set various delivery parameters. For example, the operator may set upper and lower antegrade line pressure and upper and lower retrograde line pressure (pressures at the delivery site) and an upper pressure limit at the heat exchanger. Once these values are set if the line pressure (antegrade/retrograde/heat exchanger) rises above the set limit as measured by pressure sensors appropriately placed at the delivery site, for example, pressure sensors 35, the device takes appropriate action. For example, as the pressure approaches the upper limit an alarm sounds and the pumps servo regulate to slow the delivery rate to properly adjust the pressure. Once the pressure exceeds the limit an alarm sounds, the pressure display on the remote display panel 34 flashes and pump flow will stop. If line pressure decreases pump flow restarts and the flow rate is automatically adjusted lower so that line pressure does not exceed the upper pressure limit. Flow returns to the set value and the alarm stops when line pressure returns to pre-alarm levels. In some circumstances automatic control of the pumps by the pressure control feature may not be desired. Therefore, control of the pumps may be disabled by pressing an override pushbutton 52. Additionally, the operator may choose whether to use the antegrade or retrograde pressure limits by selecting antegrade pushbutton 60 or retrograde pushbutton 62. All audible alarms may be disabled by selecting audio disable pushbutton 64. During operation if line pressure (antegrade or retrograde) falls below the lower pressure limit an audible alarm sounds and the pressure display on the remote display panel flashes. Pump speed/flow rate is not adjusted when the lower pressure limit is reached or exceeded. The alarm stops when line pressure rises above the lower pressure limit.

b. Temperature Control

The operator may choose to deliver warm water or cool water to the heat exchanger by depressing warm pushbutton 54 or cool pushbutton 56. If warm water is chosen the operator is able to select a warm water temperature setting within a range of from 4° C. to 40° C. by selecting the appropriate menu page and line on the LCD display and adjusting the setting as described above. This determines the temperature of the water that is delivered to the heat exchanger when warm pushbutton 54 is selected.

Depending on the efficiency of the heat exchanger the temperature of the blood passing through the heat exchanger will approximate the warm water temperature that has been set. The temperature of the cool water delivered to the heat exchanger is dependent upon the temperature of the cold water reservoir (ice bath). By making an appropriate selection from the LCD display 36 the operator may set a cold water temperature upper limit. This is the limit which the operator considers to be too warm for cold cardioplegia (or blood) delivery. If the upper limit is exceeded an audible signal may be sounded to warn the operator so that more ice may be added to the reservoir. The temperature of the water is displayed on LED display 58.

c. Delivery Ratios

The operator may also use the LCD display to adjust the blood to crystalloid ratio. By selecting the appropriate line and using up and down pushbuttons 48 and 50 the ratio may be adjusted in incremental steps from 0/1 (all crystalloid) to 1/0 (all blood). The increments may be chosen to provide a desired selection of variable ratios. In the preferred embodiment the ratios may be 0/1, 1/1, 2/1 . . . 16/1, 1/0. As shown in FIG. 10, the selected ratio is sent from the control panel to communication controller 107 which passes the information to the blood pump and crystalloid pump controllers. The pump controllers automatically set the rotational speed of the roller pumps so that the desired ratio is delivered.

d. Flow Rate Control

The control panel also contains the pump flow controls. The rate of total flow of cardioplegia fluid (blood and cardioplegia solution) pumped from the device is controlled by flow control dial 66 and displayed at LED 76. ump flow rate may be set by the operator from 0 to 600 mL/min. Pushbuttons 68, 70, and 72 may be used to select a counterclockwise, neutral (stop) or clockwise rotation of the blood and crystalloid pumps. By making the appropriate flow rate setting and selecting the ratio of blood to cardioplegia solution as described above, the device is capable of delivering a constant flow of cardioplegia fluid at the desired ratio.

Cardioplegia Delivery Options

The control panel also includes controls to provide for alternate cardioplegia delivery options. These include a pushbutton 74 for pulsatile flow selection and control knob 78 for setting intermittent cardioplegia delivery based upon a selected cycle length. In the embodiment disclosed the cycle length is 5 minutes.

As previously discussed, the operator may select a constant flow rate and ratio of blood to cardioplegia solution for delivery to the patient. Alternatively, several other delivery options exist. The operator may select intermittent flow or pulsatile flow, examples of which are illustrated by the flow graphs shown in FIGS. 11 and 12.

Figure 11:
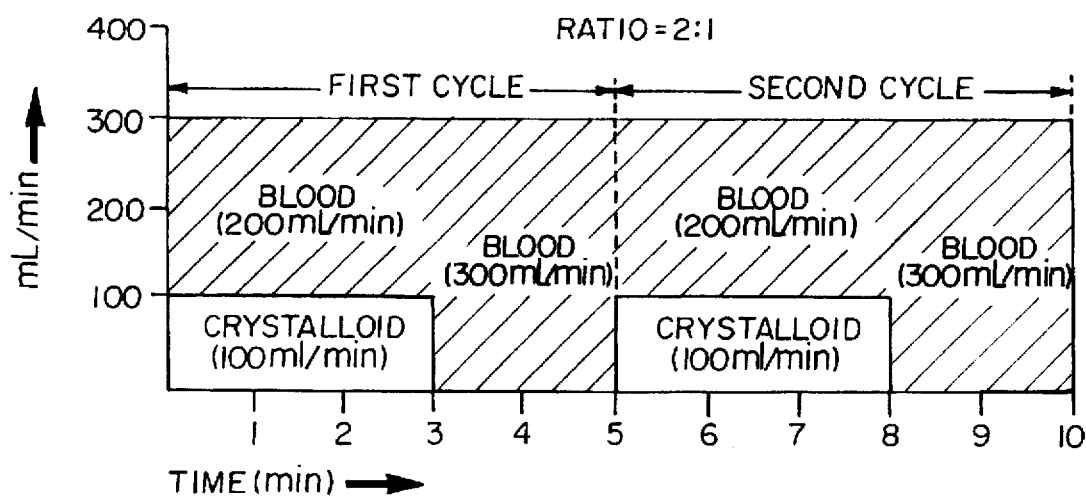
FIG. 11 is a graph illustrating intermittent delivery of cardioplegia fluid.

Intermittent cardioplegia is the mixing of crystalloid with blood at regular, repeating intervals separated by intervals where only blood is pumped. Such a delivery sequence is illustrated in FIG. 11. In this example the blood to crystalloid ratio is set at 2:1, the flow rate is set at 300 mL/min. and intermittent delivery control knob 78 is set to 3. This means that during the first three minutes of a five minute cycle crystalloid and blood (cardioplegia fluid) are being pumped. During the remaining two minutes of the cycle blood only is pumped. Total flow remains at a constant 300 mL/min. throughout the five minute cycle. This is accomplished by conveying the control signals to the pump controllers (FIG. 10) which vary the RPM of the blood and crystalloid pumps as required to achieve the flow shown in FIG. 11.

Pulsatile flow is the altering of RPM's (flow rates) of the blood and crystalloid pumps in order to create a cyclical pressure wave in the cardioplegia fluid delivered from the device. The pulsatile flow mode is actuated by selecting pulsatile flow pushbutton 74. The pump controllers are programmed with preset pulsatile flow parameters which include:

Pulse Rate: 60 cycles/minute
Base Flow: 10% of the set flow

Systolic Phase: ⅔ of cycle
Diastolic Phase: ⅓ of cycle

Figure 12:
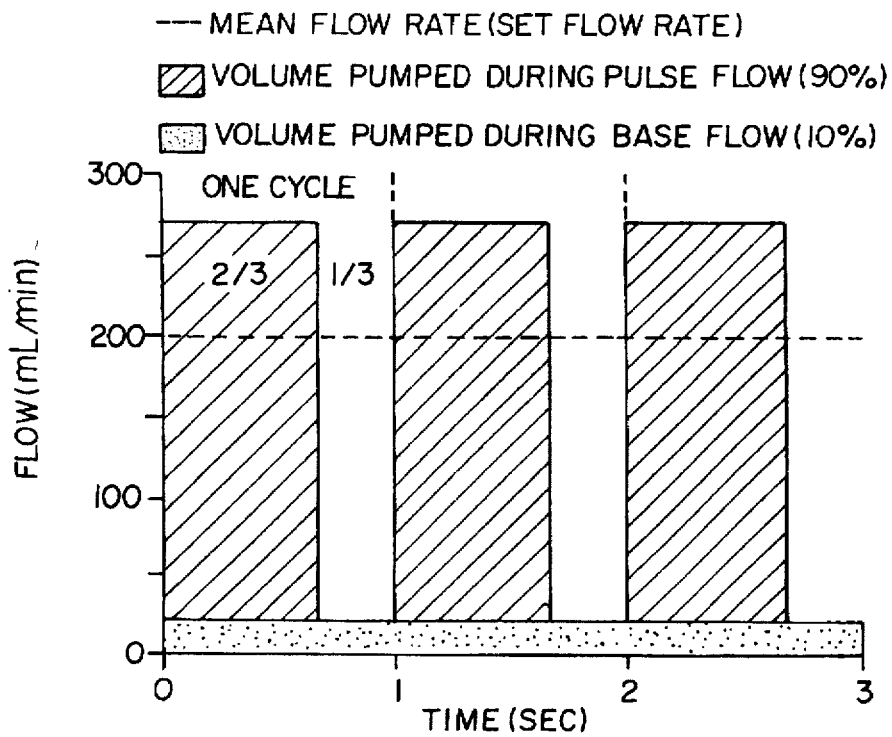
FIG. 12 is a graph illustrating pulsatile delivery of cardioplegia fluid.

The pulse rate is a default rate which may be reprogrammed by the operator. The other preset parameters are not programmable. An example of pulsatile flow mode is shown in FIG. 12. In this example flow control dial 66 is set at 200 mL/min. The mean flow across a cycle is equal to the set flow rate. Thus, in order to achieve this overall flow rate in the pulsatile mode the pumps must operate at a flow rate higher than the set flow rate during the systolic phase of the cycle as illustrated in FIG. 12.

We claim:

1. A variable ratio delivery device for delivering blood from a blood source and cardioplegia solution from a cardioplegia solution source, the blood and cardioplegia solution being combined in a selected ratio for delivery to a patient, the device comprising:

a first pump having an inlet connected to the cardioplegia solution source to cause cardioplegia solution to flow through the first pump and having an outlet connected to a cardioplegia solution supply line;

a second pump having an inlet connected to the blood source to cause blood to flow through the second pump and having an outlet connected to a blood supply line;

a delivery line connected to receive cardioplegia solution from the cardioplegia solution supply line and blood from the blood supply line; and a pump controller for adjusting the rate of flow of cardioplegia solution through the first pump and the rate of flow of blood through the second pump until the selected ratio of blood and cardioplegia solution is supplied to the delivery line.

2. The device of claim 1 further including a pressure sensor for sensing a pressure of the combined blood and cardioplegia solution at a site of delivery to the patient.

3. The device of claim 2 wherein the pressure sensor senses an antegrade pressure and whereto the prop controller may be programmed with a high antegrade pressure upper limit and wherein the pump controller is responsive to a sensed pressure which is above the upper limit to do at least one of adjusting the rate of flow through at least one of the first and second pumps, stopping at least one of the first and second pumps, or sounding an alarm.

4. The device of claim 2 wherein the pressure sensor senses an antegrade pressure and wherein the pump controller may be programmed with a low antegrade pressure lower limit and wherein the pump controller is responsive to a sensed pressure which is below the lower limit to do at least one of adjusting the rate of flow through at least one of the first and second pumps, stopping at least one of the first and second pumps, or sounding an alarm.

5. The device of claim 2 wherein the pressure sensor senses a retrograde pressure and wherein the pump controller may be programmed with a high retrograde pressure upper limit and wherein the pump controller is responsive to a sensed pressure which is above the upper limit to do at least one of adjusting the rate of flow through at least one of the first and second pumps, stopping at least one of the first and second pumps, or sounding an alarm.

6. The device of claim 2 wherein the pressure sensor senses a retrograde pressure and wherein the pump controller may be programmed with a low retrograde pressure lower limit and wherein the pump controller is responsive to a sensed pressure which is below the lower limit to do at least one of adjusting the rate of flow through at least one of the first and second pumps, stopping at least one of the first and second pumps, or sounding an alarm.

7. The device of claim 2 wherein the pump controller may be programmed with a desired pressure valve and wherein the pump controller is responsive to a sensed pressure to adjust the rate of flow through at least one of the first and second pumps in order to adjust the sensed pressure to the desired valve.

8. A device for delivering a selected ratio of blood from a blood source and cardioplegia solution from a cardioplegia solution source to a heat exchanger for delivery to a patient and for providing temperature controlled heat exchange liquid to circulate through a heat exchange liquid flow path of the heat exchanger for controlling the temperature of the blood and cardioplegia solution mixture provided to the patient, the device comprising:

a first pump having an inlet connected to receive cardioplegia solution from the cardioplegia source and an outlet connected to a cardioplegia solution supply line;

a second pump having an inlet connected to receive blood from the blood source and an outlet connected to a blood supply line;

a delivery line connected to receive cardioplegia solution from the cardioplegia supply line and blood from the blood supply line and to deliver a combined blood and cardioplegia solution mixture to the heat exchanger;

a pump controller for adjusting the rate of flow of the cardioplegia solution through the first prop and the rate of flow of blood through the second pump until the selected ratio of blood and cardioplegia solution is supplied to the delivery line;

a reservoir to hold cooled heat exchange liquid;

a heater having an inlet connected to receive heat exchange liquid from the reservoir and an outlet connected to a heat exchange liquid inlet of the heat exchanger;

a valve having an input connected to receive heat exchange liquid from a heat exchange liquid outlet of the heat exchanger and having a first outlet connected to the reservoir and a second outlet connected to deliver heat exchange liquid to the input of the heater, the valve being controllable such that either of such first and second outlets is selectable; and a pump connected to move heat exchange liquid from the reservoir through the heater and heat exchanger and back to the reservoir when the first outlet of the valve is selected and to recirculate heat exchange fluid through heater and heat exchanger when the second outlet of the valve is selected.

9. A method for delivering a desired ratio of cardioplegia solution and blood to a patient comprising:

providing a source of cardioplegia solution;

providing a source of blood;

connecting the source of cardioplegia solution to an inlet of a first pump having a variable flow rate;

connecting an outlet of the first pump to a cardioplegia supply line;

connecting the source of blood to an inlet of a second pump having a variable flow rate;

connecting an outlet of the second pump to a blood supply line;

connecting a patient delivery line to receive and combine cardioplegia solution from the cardioplegia supply line and blood from the blood supply line:

adjusting the flow rates of the first and second pumps to provide the desired ratio of cardioplegia solution and blood to the patient delivery line; and delivering the combined blood and cardioplegia solution to the patient.

* * * * *